United States Patent
Barnikol

[11] Patent Number: 5,979,229
[45] Date of Patent: Nov. 9, 1999

[54] PROCESS AND APPARATUS FOR DETERMINING THE VISCOSITY OF MICROLITER SAMPLES

[76] Inventor: Wolfgang Barnikol, Lanzelhohl 66, D-55128 Mainz, Germany

[21] Appl. No.: 08/478,881

[22] Filed: Jun. 7, 1995

[30] Foreign Application Priority Data

Jun. 18, 1994 [DE] Germany .............................. 44 21 423

[51] Int. Cl.⁶ .................................................. G01N 11/08
[52] U.S. Cl. ............................................................. 73/54.09
[58] Field of Search .................. 73/54.05, 54.06, 73/54.04, 54.09

[56] References Cited

U.S. PATENT DOCUMENTS

| 4,793,174 | 12/1988 | Yau | ..................................... 73/54.05 X |
| 4,876,882 | 10/1989 | Yau | ..................................... 73/54.05 X |

FOREIGN PATENT DOCUMENTS 282077  8/1990  Germany ................................ 73/54.06
63-313032 12/1988 Japan ..................................... 73/54.04

*Primary Examiner*—Michael Brock
*Attorney, Agent, or Firm*—Keil & Weinkauf

[57] ABSTRACT

A process for determining the viscosity of liquids on a microliter scale, wherein first the difference (a) in the pressure drop in a reference liquid flowing in a constant volume flow through a capillary measuring tube is determined with and without a sample loop inserted in the capillary measuring tube passage, the sample loop is filled with the liquid to be measured outside the capillary measuring tube passage, the sample loop is reinserted into the capillary measuring tube passage and the pressure drop is measured immediately following the insertion of the sample loop in the capillary measuring tube passage. The difference (b) in the pressure drop immediately following insertion of the sample loop and the pressure drop across the capillary measuring tube without the sample loop can then be calculated. The ratio of b to a is the relative viscosity of the liquid to be measured, from which, if the viscosity of the reference liquid is known, the absolute viscosity of the liquid to be measured can be calculated. A further object of the invention is a device for executing this process.

7 Claims, 4 Drawing Sheets

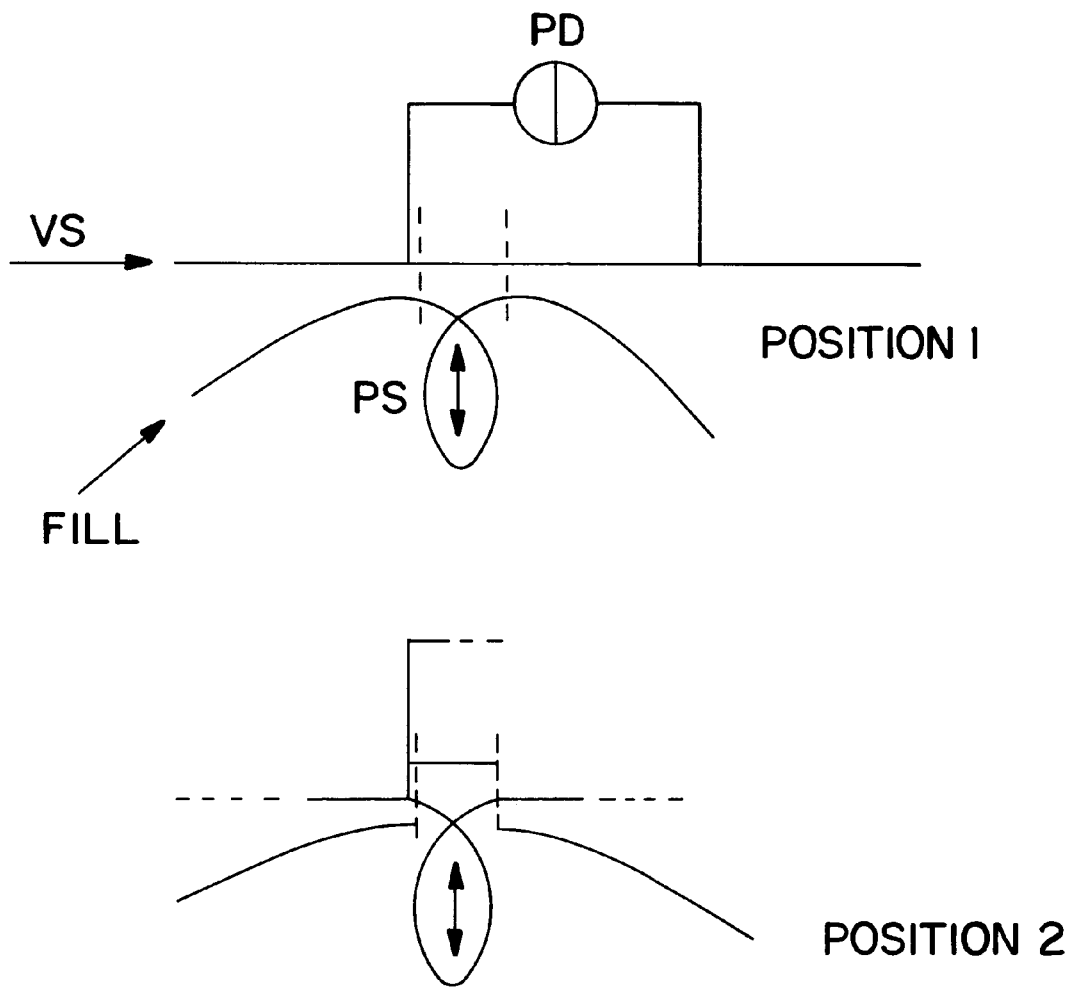
F I G. I

PROCESS AND APPARATUS FOR DETERMINING THE VISCOSITY OF MICROLITER SAMPLES

The viscosity of liquids plays a large role not only in technology, such as in connection with oil in engine manufacturing, or in the natural sciences, such as in connection with the solution structure of synthetic polymers, but also in medicine. Blood has great viscosity and this constitutes a considerable part of the flow resistance encountered by the heart. However, not only the viscosity of all of the blood is of interest, but also—for diagnostic reasons—the viscosity of the plasma by itself, i.e. that part of the blood which does not contain any cells. Viscosity is also of interest functionally, since in contrast to the large vessels of the organism, mostly plasma passes through the capillaries which are the exchange vessels of the tissue.

A particular interest of medicine in the measurement of viscosity exists in connection with the development of plasma expanders and artificial oxygen carriers, the latter as a universal replacement for stored blood. Together with the blood, such agents for aiding the functions of the blood naturally will have to have a viscosity in accordance with the norm.

As a rule, in the cited fields of application of technology and the natural sciences there is a sufficiently large sample volume available, so that all known methods for determining the viscosity of the liquids can be employed.

However, this situation is completely different in medicine. The production of artificial oxygen carriers, for example, is very expensive, and if it can be done on a milliliter scale, this means an enormous increase in the effectiveness of research, i.e. savings of time and money. There are now micro-methods in all measuring methods for the in vitro characterization of such solutions—except for determining the viscosity: the so-called micro-method of Ubbelohde requires a sample volume of approximately 3 ml, the volume requirements of the known cone-plate viscosimeter are estimated to be similar.

However, a microliter method is not only needed in vitro, but at least to the same extent for ex vivo situations. Solutions, once they have been produced and characterized in vitro, are evaluated in animal tests. However, 3 ml samples can only be collected from large animals, for example dogs, a single 3 ml sample taken from a rat would already cause the animal to go into so-called volume deficiency shock.

Furthermore, even dogs as test animals make the preparation of the solution to be tested necessary on a liter scale, which can make the research and development of this type of products ineffective, not to mention ethical objections to (unnecessary) tests on large animals.

Finally, it would be of great interest diagnostically if it were possible to determine the viscosity of the blood itself or that of the plasma by means of capillary blood from the ear lobe.

As these observations show, a necessity for a process for determining the viscosity on a microliter scale exists in medicine for many reasons.

There is of course the possibility to fill a suitable capillary tube, whose pressure drop can be measured by means of an electric pressure gauge and which is fed with a constant flow of liquid, with material to be measured via a sample inlet valve and to determine its viscosity in this way. However, all arrangements of this type have the disadvantage that for rinsing, volumes in the milliliter range are required in order to feed a capillary measuring tube completely with the undiluted material to be measured.

This and other disadvantages are removed by the measuring process in accordance with the invention for determining the viscosity of liquids on a microliter scale. It consists in that first the difference (a) in the pressure drop in a reference liquid flowing in a constant volume flow through a capillary measuring tube is determined with and without a sample loop inserted in the capillary measuring tube passage, the sample loop is filled with the liquid to be measured outside the capillary measuring tube passage, the sample loop is reinserted into the capillary measuring tube passage and the pressure drop is measured immediately following the insertion of the sample loop in the capillary measuring tube passage SP. The difference (b) in the pressure drop immediately following insertion of the sample loop (SP) and the pressure drop across the capillary measuring tube without the sample loop($S_1$) can then be calculated. The ratio of b to a is the relative viscosity of the liquid to be measured, from which, if the viscosity of the reference liquid is known, the absolute viscosity of the liquid to be measured can be calculated.

A medium which dissolves the liquid to be measured or mixes with it, as well as any other medium, can be used as reference liquid. If a liquid of known viscosity is used as reference, such as water, it is not even necessary to determine its viscosity separately and the calculation of the absolute viscosity of the liquid to be measured is very much simplified.

A decisive advantage of the measuring process in accordance with the invention is that, on the one hand, no calibration of the device for measuring the pressure drop is necessary, instead the respective measuring signal per se can be used directly, independently of its nature. However, it is important that the measurement of the pressure drop in the liquid to be measured is performed immediately following the insertion of the sample loop into the capillary measuring tube passage.

With a suitable size of the cross section of the capillary tube, the amounts of liquid required for a viscosity determination are extremely small and lie in ranges below 100 microliters.

BRIEF DESCRIPTION OF THE FIGURES

FIG. 1 is a device for determining the viscosity of microliter samples.

FIG. 1A is a preferred embodiment of the instant invention.

DETAILED DESCRIPTION OF THE INVENTION

A device suitable for performing the process in accordance with the invention is schematically represented in FIG. 1. It consists of a capillary measuring tube which can be fed with a constant volume flow (VS). The pressure drop along the capillary measuring tube can be determined by means of a suitable measuring device, for example an electric pressure gauge (PD). A sample loop (PS) can be inserted into the capillary measuring tube passage by means of suitable valves, so that two states will result: in position 1 the sample loop (PS) is not a part of the capillary measuring tube, but it can be filled with material to be measured, but in position 2 the sample loop constitutes a part of the capillary measuring tube.

Figure 2A:
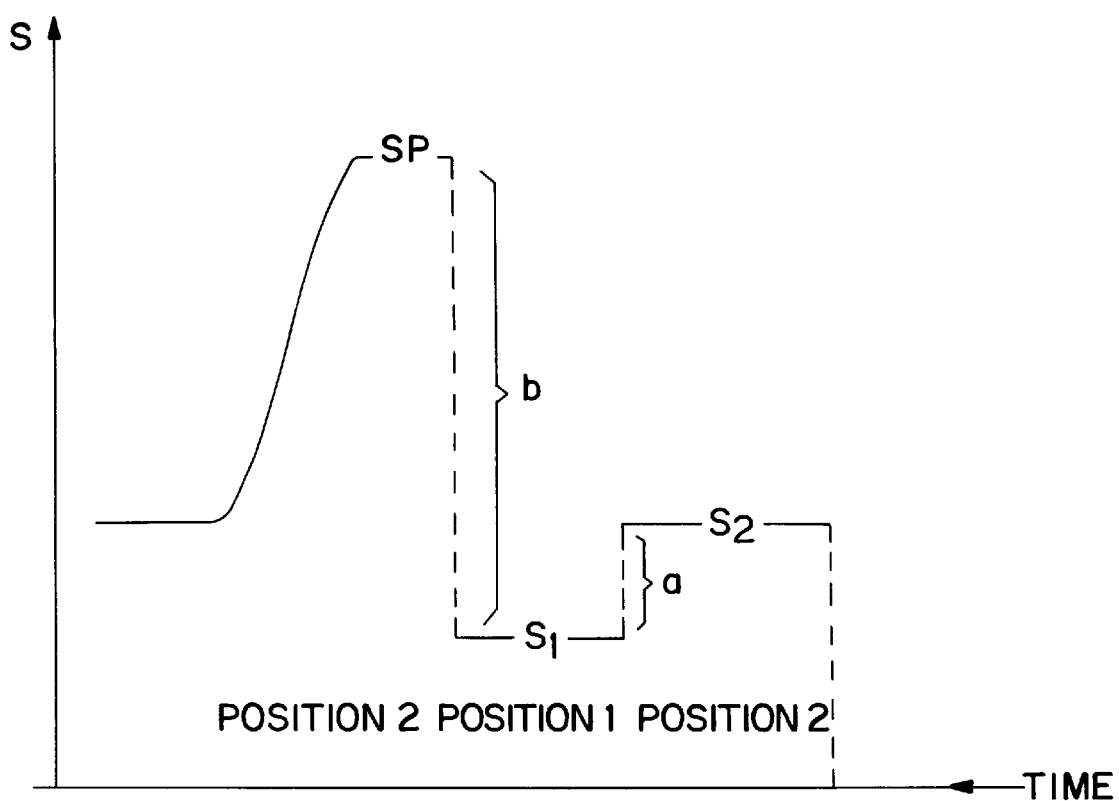
FIGS. 2a and 2b show the signal generated as a function of time.

For measuring a liquid, the following course of the signal (S) of the electric pressure gauge (PD) appears (see also the schematic representation FIG. 2a): first, the valve is in position 2 and a reference liquid at a constant volume flow VS flows through the capillary measuring tube, including the sample loop. The corresponding pressure signal (S2) is obtained. Then the valve is brought into position 1 and the sample loop is therefore removed from the capillary measuring tube passage and the pressure signal (S1) is obtained. In the meantime the loop can be filled with the liquid to be measured. After changing the valve again to position 2, the pressure signal (SP) is obtained at the beginning and then rapidly returns asymptotically to the value of the signal (S2). The measured results are schematically represented in FIG. 2a as a function of time.

The ratio of the distances (b/a) is equal to the relative viscosity (eta/eta$_0$), from which, if the viscosity of the reference liquid is known, the absolute viscosity of the liquid to be measured can be easily calculated by means of the equation $$eta_{sample} = b/a \times eta_{reference}$$

Figure 2B:
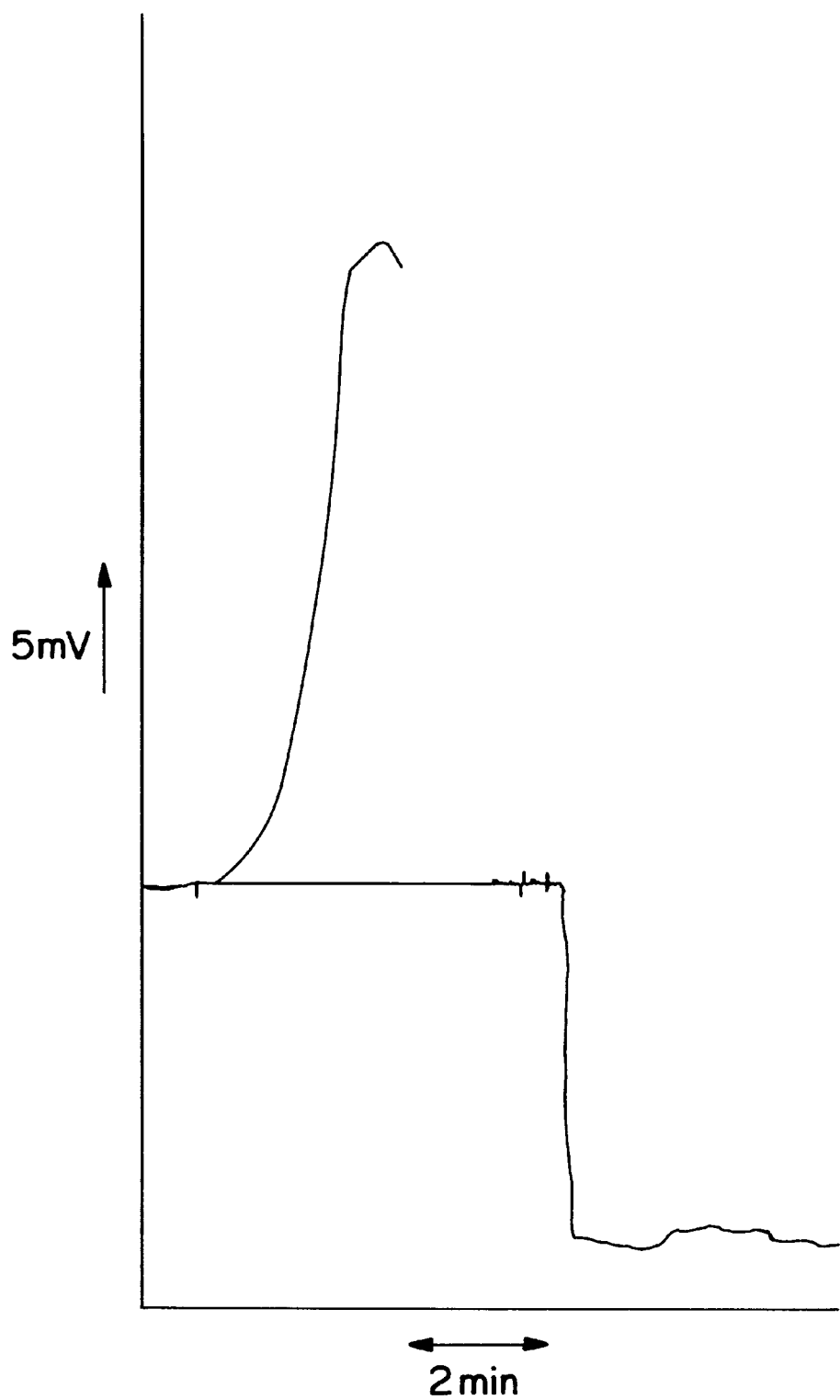

In an actual arrangement, VS equalled 60 microliters/min, the capillary measuring tube was a capillary tube of 35 cm length and 0.7 mm interior diameter, the sample loop has a length of 20 cm and the same interior diameter. An approximately 5% aqueous glycerine solution was measured. The original registration corresponding with FIG. 2a is shown in FIG. 2b.

Figure 3:
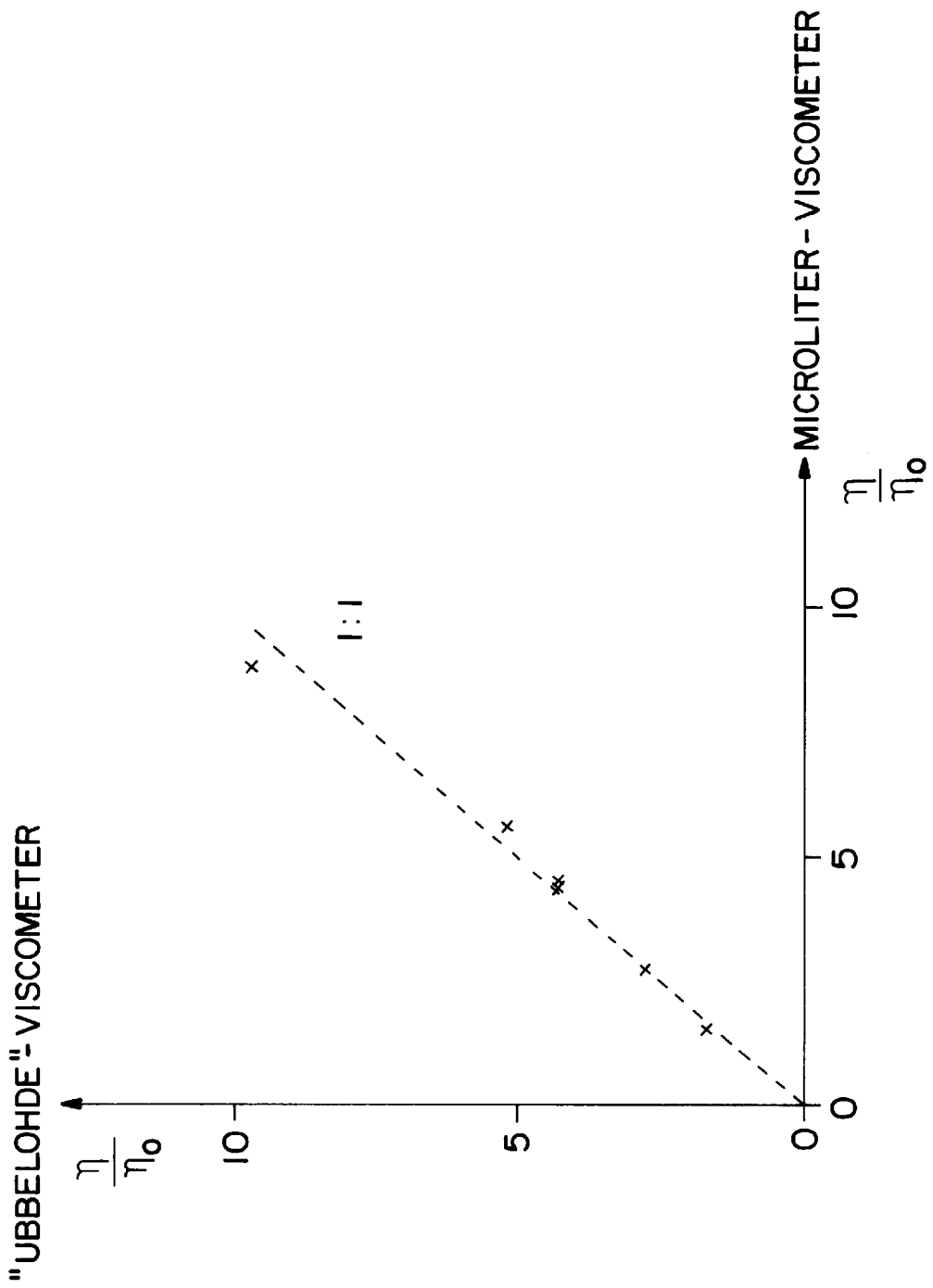
FIG. 3 shows the results of measurements comparing the results obtained by the instant invention with a conventional process.

Furthermore, comparative measurements of glycerine-water mixtures were performed at 22° C., using this novel process and the classical viscosimetry of Ubbelohde. 0.3 mm capillary tubes were employed for this. The volume flow was 0.1 ml/min and the volume requirement of the sample 55 microliters. FIG. 3 shows the results of the comparative measurements; within the framework of the measuring error there is complete agreement between the two different measurement processes.

The novel process is mainly characterized in that the actual measurement value detection of the viscous solution takes place at the time zero, a so-called zero-time method or initial value process. The process is furthermore characterized in that sample volumes of less than 60 microliters are required for measuring the viscosity. It is furthermore possible to employ capillary tubes of different interior diameters and different length.

In a preferred embodiment an electric micro pressure gauge is used as pressure detector. It is also a characteristic of the process that no calibration of the pressure gauge is required for measuring the relative viscosity; only a signal which is proportional to the pressure is required.

Since ample pure reference liquid is available as a rule, it is possible to determine the viscosity of the pure reference liquid, unless it is already known, following the determination in accordance with the invention of the relative viscosity, and then to calculate with the aid of the relative viscosity previously determined by means of the novel process the absolute viscosity of the solution to be measured in accordance with the previously mentioned equation.

Numerous designs for inserting the sample loop into a capillary measuring tube passage and filling the sample loop with the material to be measured are conceivable in connection with the device in accordance with the invention for performing the novel measuring process. In a preferred embodiment, a six-channel injection valve is used as the valve for switching the capillary tubes, which has all required change-overs and in- and outlets required for the measuring process in accordance with the invention. FIG. 1A shows the six-channel injection valve of the preferred embodiment.

I claim:

1. A process for determining the viscosity of liquids on a microliter scale, characterized in that
   (1) a difference (a) in the pressure drop across a capillary measuring tube passage in a reference liquid flowing in a constant volume flow through the capillary measuring tube passage is determined with and without a sample loop inserted in the capillary measuring tube passage,
   (2) the sample loop is filled with a liquid to be measured outside the capillary measuring tube passage,
   (3) the sample loop is reinserted into the capillary measuring tube passages, a pressure change (SP) is measured immediately following the insertion of the sample loop in the capillary measuring tube passage, and a difference (b) in the pressure change (SP) across the capillary measuring tube with the sample loop and a pressure drop ($S_1$) across the capillary measuring tube without the sample loop is determined, and
   (4) from the relative viscosity of the liquid to be measured determined as the ratio (b):(a) and the viscosity of the reference liquid, the absolute viscosity of the liquid to be measured is determined by means of the equation $$eta_{sample} = b/a \times eta_{reference}.$$

2. A process in accordance with claim 1, characterized in that water is used as the reference liquid.

3. A process in accordance with claim 1 or 2, characterized in that the sample loop has a of a volume of less than 100 microliters.

4. A device for determining the viscosity of liquids on a microliter scale, comprising
   (1) a capillary measuring tube,
   (2) a sample loop which can be inserted into a capillary measuring tube passage,
   (3) a device for inserting the sample loop into the capillary tube passage and for filling the sample loop with a liquid to be investigated outside of this capillary measuring tube passage, and
   (4) a measuring device for measuring a pressure drop across the capillary measuring tube passage.

5. A device in accordance with claim 4, characterized in that the capillary measuring tube and the sample loop have interior diameters of less than 1 mm.

6. A device in accordance with claim 4 or 5, characterized in that the volume of the sample loop is less than 100 microliters.

7. A device in accordance with claim 4, characterized in that the device for inserting and filling the sample loop consists of a six-channel injection valve.

* * * * *